(12) United States Patent
Wang et al.

(10) Patent No.: US 6,579,435 B2
(45) Date of Patent: Jun. 17, 2003

(54) GAS SENSOR

(75) Inventors: Da Yu Wang, Troy, MI (US); Paul C. Kikuchi, Fenton, MI (US); Walter T. Symons, Grand Blanc, MI (US); Kaius K. Polikarpus, Grand Blanc, MI (US); Larry M. Oberdier, Royal Oak, MI (US)

(73) Assignee: Delphi Technologies, Inc., Troy, MI (US)

( * ) Notice: Subject to any disclaimer, the term of this patent is extended or adjusted under 35 U.S.C. 154(b) by 155 days.

(21) Appl. No.: 09/740,352

(22) Filed: Dec. 18, 2000

(65) Prior Publication Data

US 2002/0108871 A1 Aug. 15, 2002

(51) Int. Cl.[7] .............................................. G01N 27/407
(52) U.S. Cl. ........................ 204/425; 204/426; 204/427; 204/429; 205/781; 205/784; 205/787
(58) Field of Search .................................. 204/421–429

(56) References Cited

U.S. PATENT DOCUMENTS

| | | | |
|---|---|---|---|
| 4,158,166 A | | 6/1979 | Isenberg |
| 4,798,693 A | * | 1/1989 | Mase et al. |
| 4,861,456 A | * | 8/1989 | Mase et al. |
| 4,880,519 A | * | 11/1989 | Wang et al. |
| 5,236,569 A | * | 8/1993 | Murase et al. |
| 5,505,837 A | | 4/1996 | Friese et al. |
| 5,556,526 A | * | 9/1996 | Fukaya et al. |
| 5,762,737 A | | 6/1998 | Bloink et al. |
| 6,270,639 B1 | * | 8/2001 | Lenfers et al. |
| 6,306,271 B1 | * | 10/2001 | Kato et al. |
| 6,332,965 B1 | * | 12/2001 | Sugiyama et al. |

FOREIGN PATENT DOCUMENTS

| | | |
|---|---|---|
| DE | 19827469 | 1/1999 |
| EP | 0310206 | 4/1989 |
| EP | 0880026 | 11/1998 |
| EP | 1174712 | 1/2002 |
| WO | 0057167 | 9/2000 |
| WO | 0127602 | 4/2001 |
| WO | 0129546 | 4/2001 |

OTHER PUBLICATIONS

Electrochemical Methods, p. 152–157, Allen J. Bard and Larry R. Faulkner, John Wiley and Sons, 1980.

* cited by examiner

Primary Examiner—T. Tung
(74) Attorney, Agent, or Firm—Vincent A. Cichosz

(57) ABSTRACT

A gas sensor is disclosed comprising an oxygen pump cell having at least one exterior pump electrode and at least one interior pump electrode disposed on opposite sides of a first solid electrolyte layer. An emf cell having a first and second emf electrodes and first and second reference gas electrodes are disposed on opposite sides of a second solid electrolyte layer. At least one insulating layer is in contact with the first and second emf electrodes. At least one via hole is disposed through the first solid electrolyte layer. At least one air channel is disposed through at least one insulating layer. An air vent is disposed in at least one insulating layer in contact with the first and second reference gas electrodes. A heater is disposed in thermal communication with the sensor. And at least five electrical leads are in electrical communication with said sensor. A method of using a gas sensor is also disclosed.

6 Claims, 5 Drawing Sheets

GAS SENSOR

TECHNICAL FIELD

The present invention relates to gas sensors. More particularly, the present invention relates to an exhaust gas sensor.

BACKGROUND

Exhaust sensors are used in a variety of applications that require qualitative and quantitative analysis of gases. For example, exhaust sensors have been used for many years in automotive vehicles to sense the presence of exhaust gases. In automotive applications, the direct relationship between various exhaust gas concentrations and the air-to-fuel ratios of the fuel mixture supplied to the engine allows the sensor to provide concentration measurements for determination of optimum combustion conditions, maximization of fuel economy, and the management of exhaust emissions. The management of exhaust emissions has become increasingly important because of the increased use of automobile engines.

One method of sensing exhaust gas uses electrochemistry. With an electrochemical method, there are two basic principles involved in gas sensing: the Nernst principle and the polarographic principle. Typically, an exhaust gas sensor utilizing an electrochemical method comprises an electrochemical pump cell (polarographic principle) and an electrochemical motive force cell (Nernst principle).

With the Nernst principle, chemical energy is converted into electromotive force ("emf"). A gas sensor based upon this principle typically consists of an ionically conductive solid electrolyte material, a porous electrode with a porous protective overcoat exposed to exhaust gases ("sensing electrode"), and a porous electrode exposed to a known gas's partial pressure ("reference gas electrode"). Sensors typically used in automotive applications use a yttria stabilized zirconia based electrochemical galvanic cell with porous platinum electrodes, operating in Nernst mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:

$E$ = electromotive force
$R$ = universal gas constant
$F$ = Faraday constant
$T$ = absolute temperature of the gas
$P_{O_2}^{ref}$ = oxygen partial pressure of the reference gas
$P_{O_2}$ = oxygen partial pressure of the exhaust gas With the polarographic principle, the sensors utilize electrolysis whereby ions are sensed through a diffusion limiting current for aqueous electrolyte systems. The same approach can be applied to solid electrolyte systems for sensing gas species and for sensing of wide range air-to-fuel ratio of combustion exhaust gas systems. Generally, a sensor employing the polarographic principle is composed of a pair of current pumping electrodes where both are in contact with an oxide conductive, solid electrolyte and one electrode is in contact with a gas diffusion limiting means. The gas diffusion limiting means in conjunction with the pump electrodes create a limiting current which is linearly proportional to the measured gas concentration in the sample.

A known type of exhaust sensor includes a flat plate sensor formed of various layers of ceramic and electrolyte materials laminated and sintered together with electrical circuit and sensor traces placed between the layers in a known manner. In this sensor, the sensing element can be both difficult and expensive to package within the body of the exhaust sensor since it generally has one dimension that is very thin and is usually made of brittle materials. Consequently, great care and time consuming effort must be taken to prevent the flat plate sensing element from being damaged by exhaust, heat, impact, vibration, the environment, etc. This is particularly problematic since most materials conventionally used as sensing element supports, glass and ceramics for example, cannot withstand much bending. With the use of ceramic materials, thermal shock resistance is a primary concern. This has an effect of influencing sensor manufacture because of the precautions taken to preserve during the sensor's lifetime the fragile ceramic materials, i.e., to prevent cracking from thermal shocks, and the sensor's electronics for heating control and sensing.

Accordingly, there remains a need in the art for a sensor that is durable and that can be fabricated easier and at a reduced cost.

SUMMARY

The deficiencies of the above-discussed prior art are overcome or alleviated by the gas sensor and method of producing the same.

A gas sensor is disclosed comprising an oxygen pump cell having at least one exterior pump electrode and at least one interior pump electrode disposed on opposite sides of a first solid electrolyte layer. An emf cell having a first and second emf electrodes and first and second reference gas electrodes are disposed on opposite sides of a second solid electrolyte layer. At least one insulating layer is in contact with the first and second emf electrodes. At least one via hole is disposed through the first solid electrolyte layer. At least one air channel is disposed through at least one insulating layer. An air vent is disposed in at least one insulating layer in contact with the first and second reference gas electrodes. A heater is disposed in thermal communication with the sensor. And at least five electrical leads are in electrical communication with said sensor.

A method of using a gas sensor is disclosed comprising measuring a first emf value between the first emf electrode and the first reference gas electrode. Comparing the first emf value with a first pre-determined voltage value for driving a first pump current between the first exterior pump electrode and the first interior pump electrode. Measuring a second emf value between the second emf electrode and the second reference gas electrode. Comparing the second emf value with a second pre-determined voltage value for driving a second pump current between the second exterior pump electrode and the second interior pump electrode. Determining concentrations of gases by comparing values between the first emf electrode and the second emf electrode. Measuring the first pump current and the second pump current between the first exterior pump electrode and the first interior pump electrode.

A method of using a gas sensor is disclosed comprising measuring a first emf value between the first emf electrode and the first reference gas electrode. Comparing the first emf value with a first pre-determined voltage value for driving a pump current between the exterior pump electrode and the interior pump electrode. Measuring a second emf value between the second emf electrode and the second reference gas electrode. Comparing the second emf value with a second pre-determined voltage value. Determining concentrations of gases by comparing emf value between the first emf electrode and the second emf electrode. Measuring the pump current between the exterior pump electrode and the interior pump electrode.

BRIEF DESCRIPTION OF THE DRAWINGS

Referring now to the figures, which are meant to be exemplary, not limiting, and wherein like elements are numbered alike in several Figures.

DETAILED DESCRIPTION OF THE PREFERRED EMBODIMENT

Figure 1:
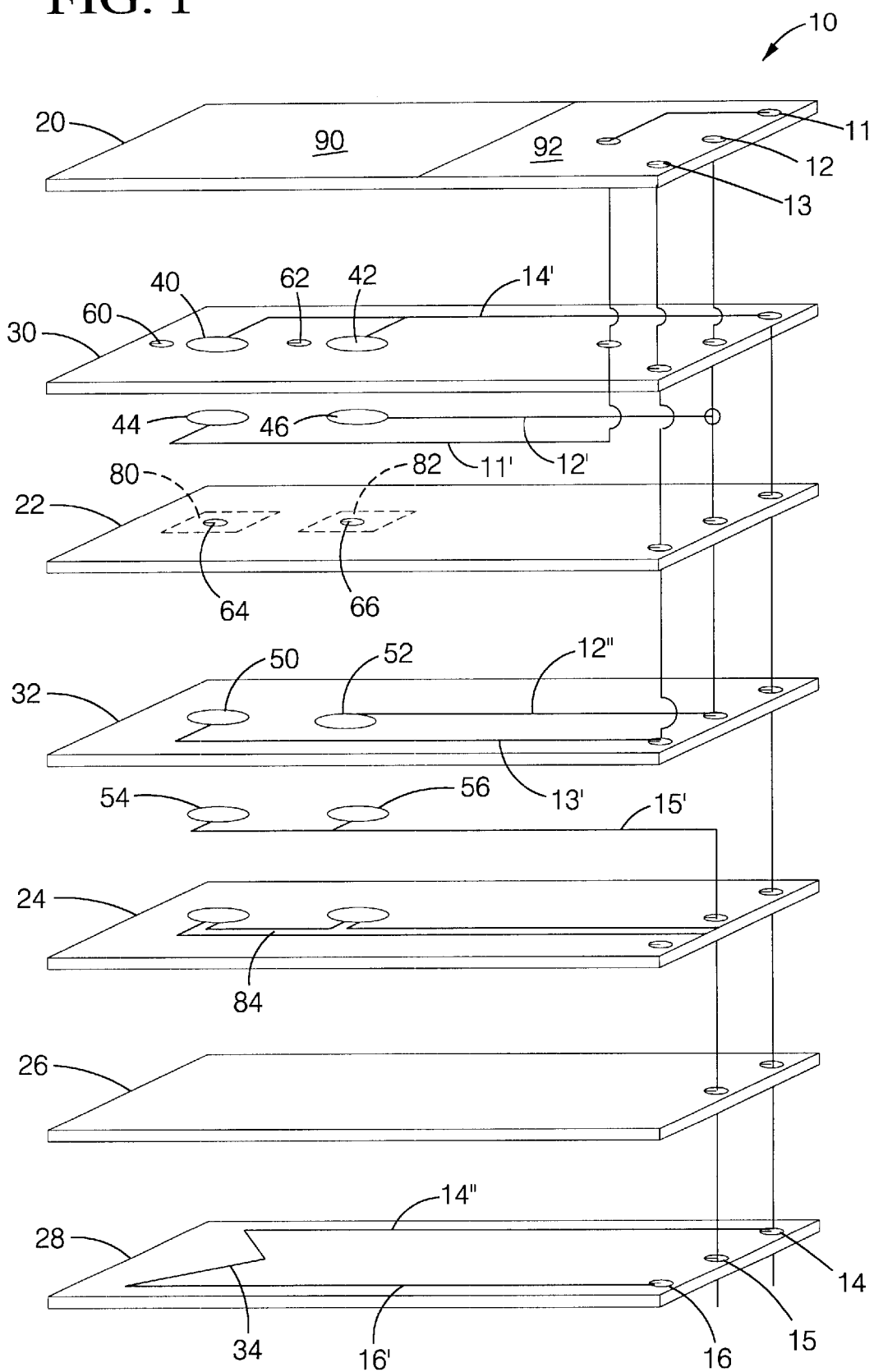
FIG. 1 is an exploded view of a sensor design with a 6-lead structure.

Referring to FIG. 1, two electrochemical cells of the sensor 10 are illustrated. The first electrochemical cell is an oxygen pump cell with two exterior pump electrodes 40, 42 and two interior pump electrodes 44, 46, disposed on opposite sides of a first electrolyte layer 30. The second electrochemical cell is an emf cell with two emf electrodes 50, 52 and two reference gas electrodes 54, 56, disposed on opposite sides of a second electrolyte layer 32.

The emf cell and pump cell are arranged in an alternating electrolyte, dielectric layer, electrolyte structure where several dielectric layers can be disposed between the electrolytes. Therefore, layers 20, 22, 24, 26, and 28 are dielectric layers that are comprised of an electrically insulating material while layers 30 and 32 are comprised of an electrolyte. Dielectric layers 22, 24, 26, and 28, are typically capable of: providing structural integrity (e.g., effectively protecting various portions of the gas sensor from abrasion, vibration, and the like, and providing physical strength to the sensor); and physically separating and electrically isolating various components. The insulating layer(s), which can be formed using ceramic tape casting methods or other methods such as plasma spray deposition techniques, screen printing, stenciling and others conventionally used in the art, can each be up to about 200 microns thick, with a thickness of about 50 microns to about 200 microns preferred. In order to reduce the leakage current, high resistance dielectric materials should be employed, e.g. materials, which at temperatures of 800° C., have a current leakage of less than 0.01 microampere. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating layer is dependent upon the specific electrolyte employed. Possible dielectric materials include alumina, lanthanum oxide, strontium oxide, titania, strontium titanate, barium titanate and the like, as well as combinations comprising at least one of the foregoing dielectric materials.

The electrolyte layers 30, 32, are preferably a solid electrolyte that can comprise the entire layer or a portion thereof, can be any material that is capable of permitting the electrochemical transfer of oxygen ions while inhibiting the physical passage of exhaust gases, has an ionic/total conductivity ratio of approximately unity, and is compatible with the environment in which the gas sensor will be utilized (e.g., up to about 1,000° C.). Possible electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing materials. For example, the electrolyte can be alumina and yttrium stabilized zirconia. Typically, the electrolyte, which can be formed by many conventional processes (e.g., die pressing, roll compaction, stenciling and screen printing, tape casting techniques, and the like), has a thickness of up to about 500 microns, with a thickness of approximately 25 microns to about 500 microns preferred, and a thickness of about 50 microns to about 200 microns especially preferred.

It should be noted that, in some embodiments, a porous electrolyte may also or alternatively be employed. The porous electrolyte should be capable of permitting the physical migration of exhaust gas and the electrochemical movement of oxygen ions, and should be compatible with the environment in which the gas sensor is utilized. Typically, porous electrolyte has a porosity of up to about 20% or so, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes that may be useful in the instant application. Possible porous electrolytes include those listed above for the solid electrolyte.

The various electrodes 40, 42, 44, 46, 50, 52, 54, and 56 are disposed on opposites sides of an in ionic contact with electrolyte layers 30, 32. These electrodes can comprise any catalyst capable of ionizing oxygen, including, but not limited to, metals such as platinum, palladium, osmium, rhodium, iridium, gold, ruthenium zirconium, yttrium, cerium, calcium, aluminum, zinc, lanthanum, strontium, cobalt, perovskite, and the like; other materials, such as silicon, and the like; as well as oxides, mixtures, alloys, and cermets comprising at least one of the foregoing catalysts. As with the electrolyte, the electrodes 40, 42, 44, 46, 50, 52, 54, and 56 can be formed using conventional techniques. Some possible techniques include sputtering, chemical vapor deposition, screen printing, painting, and stenciling, among others. If a co-firing process is employed for the formation of the sensor, screen printing the electrodes onto appropriate tapes is preferred due to simplicity, economy, and compatibility with the co-fired process. For example, reference electrode 54 can be screen printed onto insulating layer 24 or over the solid electrolyte 32, while exhaust electrode 50 can be screen printed over solid electrolyte 32 or on insulating layer 22. Electrode leads 11', 12', 12", 13', 14', 15' (as shown in FIG. 1) and vias 11, 12, 13, 14, 15, and 16 in the insulating and/or electrolyte layers are typically formed simultaneously with electrodes.

The electrodes 40, 42, 44, 46, 50, 52 are exposed to exhaust gas through an optional protective layer 20. The protective layer 20, with a porous section 90 and a dense section 92, is disposed above the pump electrodes and is comprised of a gas diffusion limiting substance, such as porous and dense alumina, spinel, as well as combinations comprising at least one of the foregoing substances. Catalyst materials or filter materials can be added to part or all of the porous section 90, especially the portion that connects to via holes 60, 62. Poison protection for the pump electrodes 40, 42, 44, 46, and the emf electrodes 50, 52 is achieved through the presence of the protective layer 20 and the design of the electrolyte layers 30, 32 and insulating layers 22, 24, 26.

To pass gas onto the emf sensing electrodes 50, 52, gas passes through the two via holes 60, 62 disposed through the first electrolyte layer 30. Thereby, the sensing emf electrodes 50, 52 are in fluid communication with the lower placed pump electrodes 44, 46 through the dielectric layer 22. Dielectric layer 22 has optional air channels 80, 82 that are comprised of a porous channel for exhaust diffusion and/or via holes 64, 66. The air channels 80, 82 are disposed through the dielectric layer 22. Gas diffusion limiting means can be provided by the protective layer 20, via holes 60, 62, 64, 66, and air channels 80, 82.

The reference gas electrodes 54, 56 are in communication with an air vent 84 connected with ambient air atmosphere. The air vent 84 is disposed within or adjacent to dielectric layer 24. Additionally or alternatively, the reference gas electrodes 54, 56 can be exposed to oxygen by having oxygen pumped into the sensor by using an oxygen pump cell (can be pumped from first emf electrode to the reference gas electrode).

Via holes 60, 62, 64, 66, air channels 80, 82, and air vent 84 are formed by depositing a fugitive material, e.g. carbon base material such as carbon black, such that upon processing the material burns out, and leaves a void. This fugitive material can be employed alone or in conjunction with an oxygen storage material. Possible oxygen storage materials include precious metals, alkaline materials, and the like, as well as combinations and alloys comprising at least one of the foregoing oxygen storage materials.

In addition to the air channels, vias, and air vent, the sensor also comprises a heater 34 to maintain sensor 10 at proper operating temperature. The heater 34 is provided on a dielectric layer 28 with one or more optional dielectric layers 26 disposed between the heater 34 and the emf cell. The heater 34 is employed to maintain the sensor element at the desired operating temperature. The heater 34 can be any conventional heater capable of maintaining the sensor end at a sufficient temperature to facilitate the various electrochemical reactions therein. The heater 34, which is typically platinum, alumina, palladium, and the like, as well as mixtures and alloys comprising at least one of the foregoing metals, or any other conventional heater, is generally screen printed onto a substrate to a thickness of about 5 microns to about 50 microns.

The heater 34 electrically communicates with the lead 14", 16'. Three leads 11'; 12'; and 14' electrically communicate with the oxygen pump cell electrodes 44; 46; and 40, 42, respectively. Three leads 12"; 13'; and 15' electrically communicate with the emf cell electrodes 52; 50; and 54, 56, respectively. The leads, which supply current to the heater and electrodes, are typically formed on the same layer as the heater/electrode to which they are in electrical communication and extend from the heater/electrode to the terminal end of the gas sensor where they are in electrical communication with the corresponding via and appropriate contact pads (not shown).

The gas sensor components, i.e., protective layers 20, electrodes 40, 42, 44, 46, 50, 52, 54, and 56 (and leads thereto), heater 34, electrolyte layers 30, 32 and dielectric layers 22, 24, 26, and 28 are conventional components in a gas sensor. Furthermore, in addition to these conventional components, additional conventional components can be employed, including but not limited to additional protective coatings (e.g., spinel, alumina, magnesium aluminate, and the like, as well as combinations comprising at least one of the foregoing coatings), lead gettering layer(s), ground plane (s), support layer(s), additional electrochemical cell(s), and the like.

The sensor comprising the above-described components can be formed in any conventional fashion, with co-firing the various components preferred.

Figure 2:
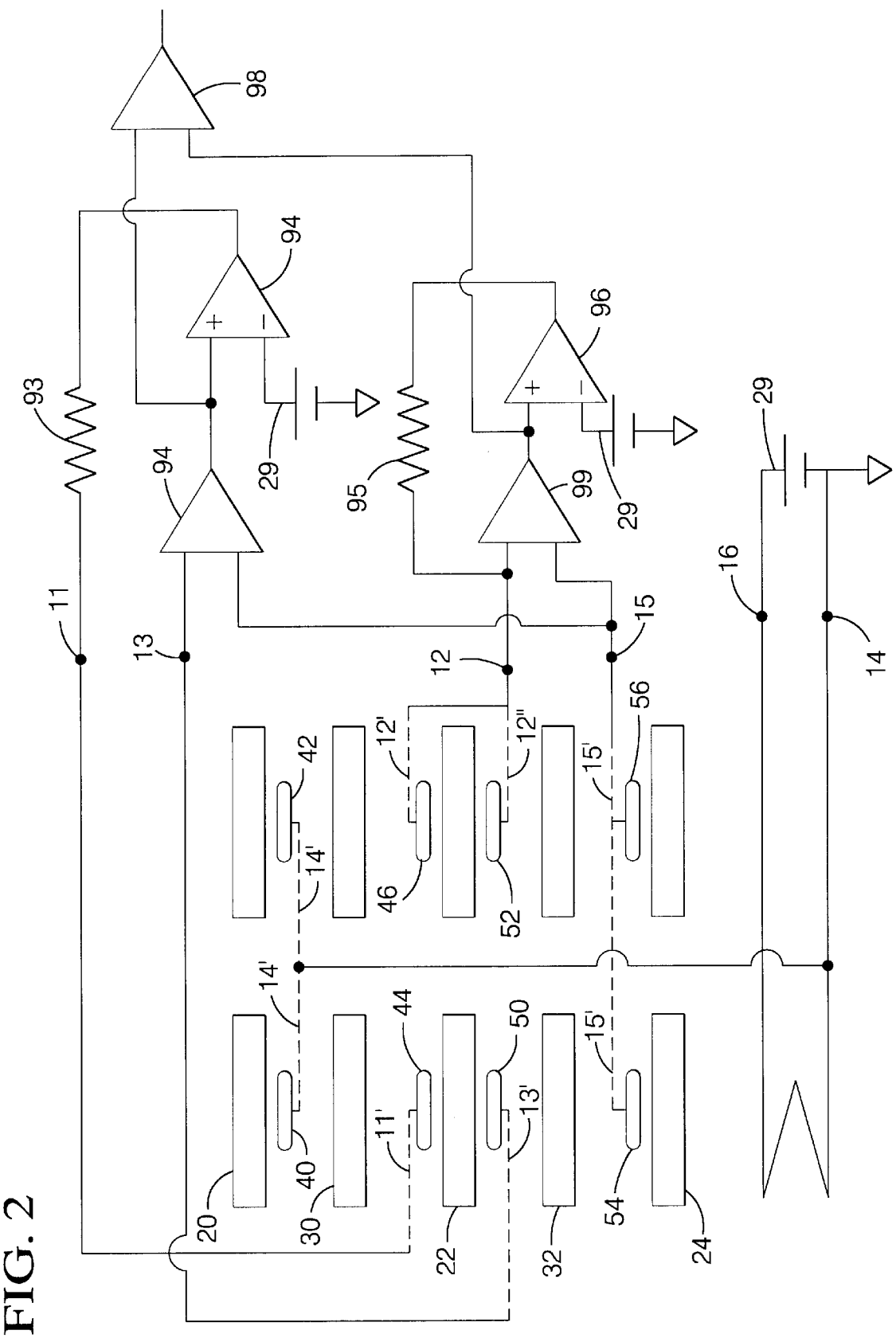
FIG. 2 is an electrical schematic of the sensor design of FIG. 1.

Referring now to FIG. 2, the sensor drive circuit for a 6-lead structure is depicted. As stated above, three leads 11', 12', and 14' electrically communicate with the oxygen pump cell electrodes 44, 46, and 40, 42, respectively. Also, three leads 12", 13', and 15' electrically communicate with the emf cell electrodes 52, 50, and 54, 56, respectively. The arrangement of the leads is not limited to this description or the illustrations in the figures.

Referring still to FIG. 2, external to the sensor electrode arrangement, lead 11 ' is in electrical communication with operational amplifier ("OP-amp") 94 with a region of resistance 93 between lead 11' and OP-amp 94. The lead 11' also communicates electrically with a power source 29. The lead 12' joins externally to the sensor electrode arrangement and electrically connects with two instrumentation amplifiers 98, 99. The lead 12' is also in electrical communication with OP-amp 96 with a region of resistance 95 between lead 12' and OP-amp 96. Both electrodes 40 and 42 are wired with the power source 29 through lead 14'. The lead 13' is electrically connected directly with an instrumentation amplier 97. One portion of the instrumentation amplifier 97 is in electrical communication with the OP-amp 94 and the other portion is wired to the instrumentation amplifier 98. The lead 14', shown as the negative lead, joins externally to the sensor electrode arrangement and is electrically connected with the power source 29. The lead 15' also connects with the instrumentation amplifier 99 and with the instrumentation amplifier 98 and OP-amp 96. The remaining lead 16' is for the heater 34 and is attached to the power source 29.

Figure 3:
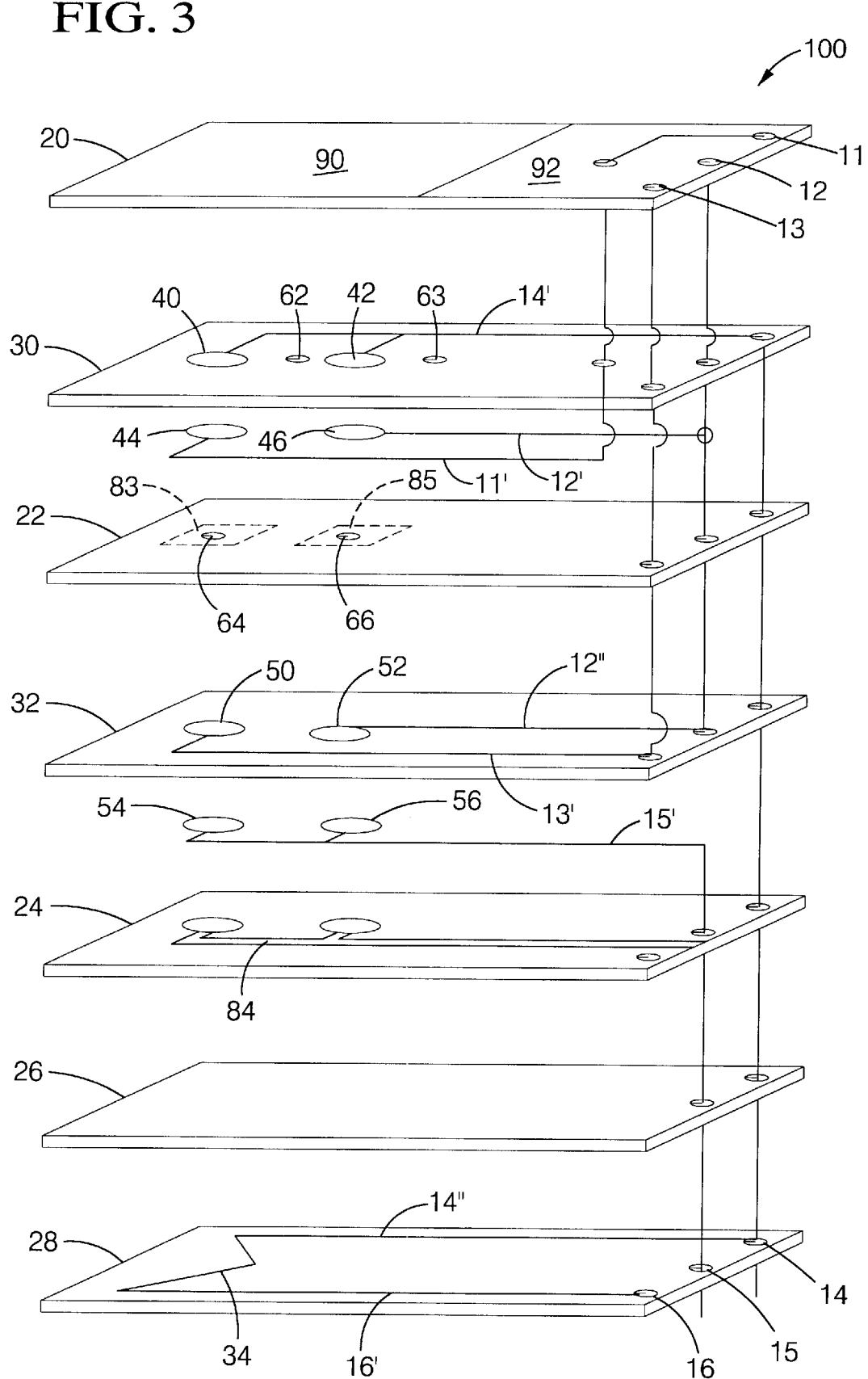
FIG. 3 is an exploded view of a sensor design with a 6-lead structure.

Referring to FIG. 3, a sensor 100 is also shown as a 6-lead device. The sensor elements, including leads, are those as discussed in FIG. 1 with the following exceptions. Via hole 63 is disposed on electrolyte layer 30 replacing via holes 60, 62 (from FIG. 1). Gas diffusion limiting can be provided by air channel 83 and/or 85 located between electrodes 44 and 46 disposed on insulating layer 22.

Figure 4:
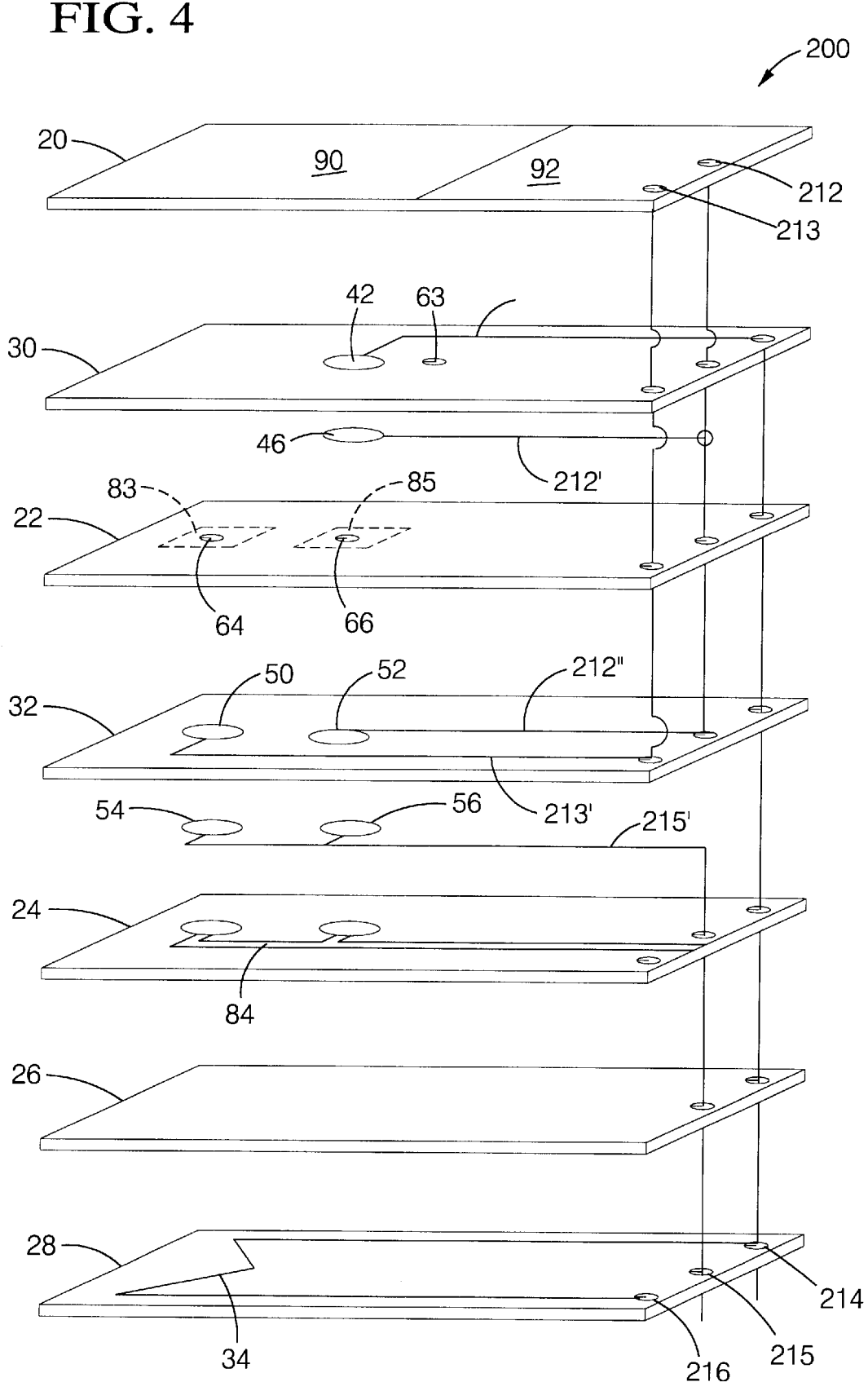
FIG. 4 is an exploded view of a sensor design with a 5-lead structure.
Figure 5:
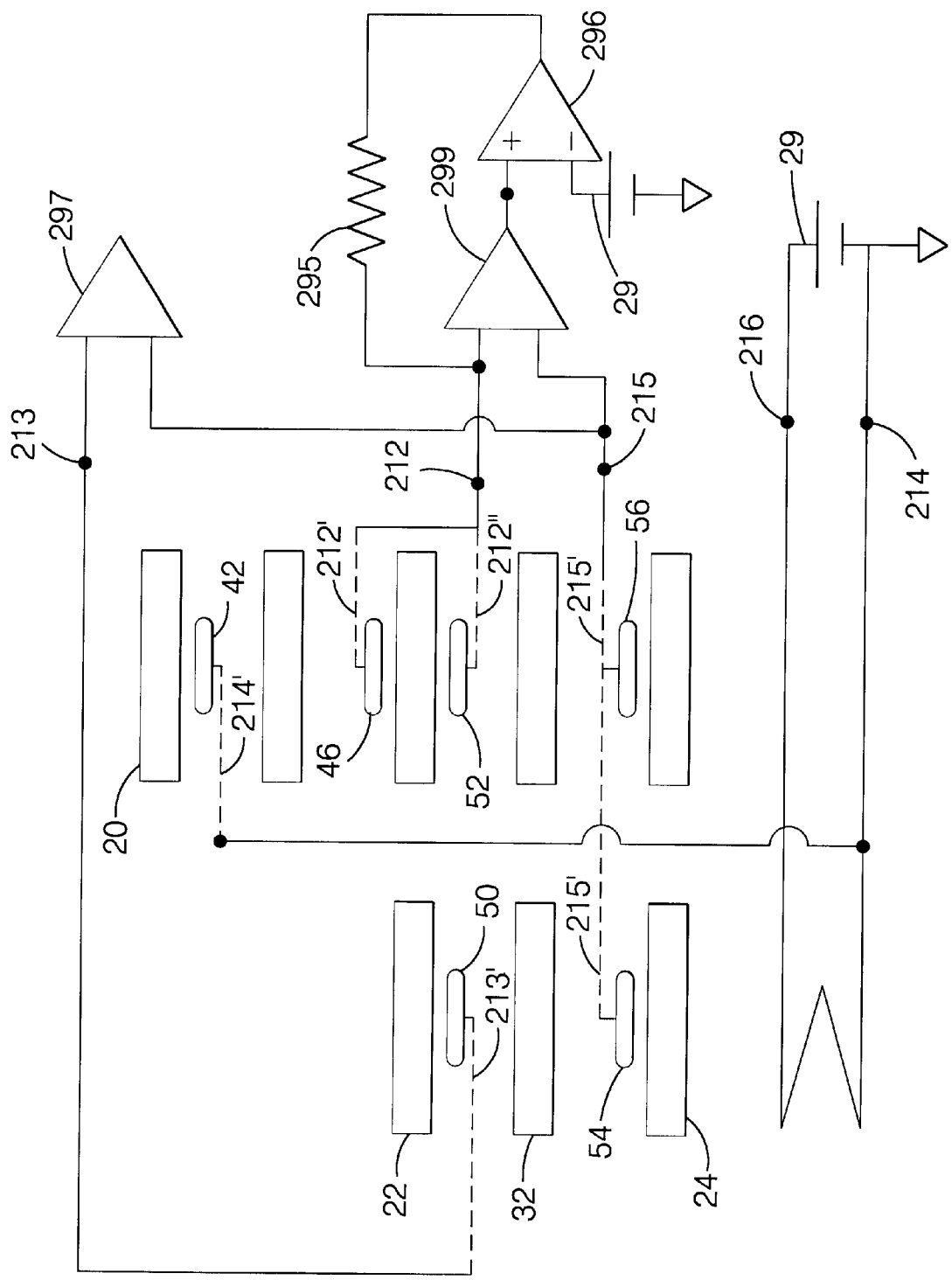
FIG. 5 is an electrical schematic of the sensor design of FIG. 4.

Referring to FIG. 4 and sensor drive circuit of FIG. 5, sensor 200 is shown as a 5-lead device. The sensor components are those as discussed in FIG. 3. One lead is removed from the 6-lead device by eliminating two oxygen pump electrodes. In FIG. 4, two leads 212', 214' electrically communicate with the oxygen pump cell electrodes 42, 46, respectively. Three leads 212"; 213'; and 215' electrically communicate with the emf cell electrodes 52; 50; and 54, 56, respectively. The remaining lead 216 is for the heater 34.

Referring still to FIG. 5, external to the sensor electrode arrangement, lead 212' joins externally to the sensor electrode arrangement and is in electrical communication with instrumentation amplifier 299. The lead 212' is also connected with an OP-amp 296 with a region of resistance 295 between the lead 212' and the OP-amp 296. The lead 213' electrically communicates directly with an instrumentation amplifier 297. One portion of the instrument amplifier 297 is in electrical communication with the lead 215'. The lead 214', shown as the negative lead, joins externally to the sensor electrode arrangement and is connected with the power source 29. The lead 215' is wired with an instrumentation amplifier 299 and the OP-amp 296. As in the 6-lead embodiment, leads 214' and 216 of the heater 34 are attached to the power source 29.

There are many different gas species in the exhaust gas mixture that can interfere with the gas sensing. Several methods are known in the art to enhance the selectivity of the sensing devices for a particular gas species. These include: a) an electrolysis method; b) maintaining the background gas concentration at a constant level (e.g. by gas pump method) that does not interfere with the sensing of the gas species; c) the use of mechanical filters or electrochemical filters; d) the use of catalytic or non-catalytic materials as the materials for the electrodes or placed near the electrodes; or e) controlling the temperature of the device such that certain (catalytic) combustible reactions can occur, the gas species becomes stable or unstable, or at which cracking, steam forming, hydrogenation, or dehydrogenation can occur.

There are several different ways to implement controlling the exhaust gas sensor for multi-gas sensing. Within the sensor are two independent electrochemical group-cells. The placement of these electrochemical group-cells is dependent upon the requirement of different temperatures during sensing. As shown in FIG. 1, the first electrochemical group-cell can be comprised of electrodes 40, 44, 50, 54 and the second electrochemical group-cell can be comprised of 42, 46, 52, 56. The following describes three separate procedures using electrochemical group-cells for multi-gas sensing.

The first procedure is described using FIG. 2. The sensor operation can be controlled with the first electrochemical group-cell 40, 44, 50, 54 using an instrumentation amplifier to measure the emf between electrodes 50 and 54. This value is compared with a pre-determined voltage value to drive a pump current between electrodes 40 and 44 until the emf value equals the pre-determined voltage value. The second electrochemical group-cell 42, 46, 52, 56 is controlled in a similar way. When using different temperatures, different catalysts, or different electrode materials between the two electrochemical group-cells, the contents of $NO_x$ or HC will also be different, even though the oxygen level is the same. For example, depending upon the placement of the heater, a controlled temperature difference between the cells can be created. One electrochemical group-cell can be controlled at a higher temperature to allow for $NO_x$ decomposition or HC oxidation reaction. At the same time, the other electrochemical group-cell can be controlled at a lower temperature to inhibit the reactions to a lesser degree. To further inhibit, or enhance, the reaction, platinum, rhodium, or the like could be used as the electrode materials for the first electrochemical group-cell 40, 44, 50, 54 while a gold-platinum alloy, or the like, could be utilized as the electrode material for the second electrochemical group-cell 42, 46, 52, 56. The concentrations of $NO_x$ or HC can be sensed by comparing the emf value between electrodes 50 and 52. The pump currents, between electrodes 40 and 44, can be used as the values for determining the air to fuel ratios of the exhaust gas.

The second procedure is described using FIG. 3. In this procedure, the first electrochemical group-cell includes one of the additional gas sensing methods outlined above (a–e) to further enhance the selectivity of sensing gases. The second electrochemical group-cell does not operate with any of the additional methods. Exhaust gas enters first into the second electrochemical group-cell and oxygen is pumped out of the exhaust gas while the sensing gas species are not affected. The oxygen deficient exhaust gas enters the first electrochemical group-cell through the gas channel connected between electrodes 44 and 46. The gas sensing signal can be measured between the two emf electrodes 50 and 52 or by the pump current of the first electrochemical group-cell. The pump current generated between electrodes 42 and 46 can be used for air to fuel ratio sensing.

The last procedure is described using FIG. 4, wherein only two pump electrodes 42, 46 are utilized. Also in this procedure, the first electrochemical group-cell includes one of the additional gas sensing methods outlined above (a–e) to further enhance the selectivity of sensing gases. The second electrochemical group-cell does not operate with any of the additional methods. Exhaust gas enters first into the second electrochemical group-cell and oxygen is pumped out of the exhaust gas while the sensing gas species are not affected. The oxygen deficient exhaust gas enters the first electrochemical group-cell through the gas channel near electrode 46. The gas sensing signal can be measured between the two emf electrodes 50 and 52 or by the pump current of the first electrochemical group-cell. The pump current generated between electrodes 42 and 46 can be used for air to fuel ratio sensing.

Other embodiments include the addition of more electrodes to the emf cell for multi-gas sensing. Another emf cell with additional diffusion limiting means can be added and connected to the existing emf cells for multi-gas sensing. Both an additional pump cell and an emf cell can be added for multi-gas sensing. Lastly, another alumina-zirconia-alumina layer structure can be added to the structure illustrated herein, as long as ionic and electronic isolation can be achieved.

The sensor design described herein can utilize one or both the Nernst emf electrochemical cells and pumping type electrochemical cells (pump cell). The sensor can be constructed with a reduced number of leads while being capable of covering a wide range of air to fuel ratios. The sensor can be designed to allow most of the electrodes to share the same exhaust gas path. With a dielectric layer, disposed between the electrolyte layers, the mechanical and thermal shock resistance properties of the sensor are increased. Further, the sensor electrodes share the same poison resistance which makes the sensor easier to fabricate and more economical. The single poison resistance feature acts in particular to allow the pump electrodes to work as a poison-getter material for the emf sensing electrodes. With the embodiments described, a more easily fabricated and durable sensor is formed with a reduced number of leads to the gas sensor resulting in reduced costs. Additionally, the composite structure of the sensor provides for mechanical and thermal shock resistance.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. A gas sensor, comprising:
   an oxygen pump cell having an exterior pump electrode and an interior pump electrode disposed on opposite sides of a first solid electrolyte layer;
   an emf cell having a first and second emf electrodes and first and second reference gas electrodes disposed on opposite sides of a second solid electrolyte layer;
   a via hole disposed through said first solid electrolyte layer;
   an air channel disposed through a first insulating layer wherein the air channel layer is in fluid communication with said first and second emf electrodes;
   an air vent disposed in at least a second insulating layer in fluid communication with said first and second reference gas electrodes;
   a heater disposed in thermal communication with said sensor; and
   at least five electrical leads in electrical communication with said sensor;
   wherein said interior pump electrode and said first and second emf electrodes are in fluid communication through said first insulating layer.

2. The gas sensor of claim 1, further comprising a protective insulating layer in contact with said exterior pump electrode.

3. The gas sensor of claim 1, wherein said five electrical leads comprises a first lead in electrical communication with said interior pump electrode and said second emf electrode, a second lead in electrical communication with said first emf electrode, a third lead in electrical communication with said exterior electrode and said heater, a fourth lead in electrical communication with said first and second reference electrodes, and a fifth lead in electrical communication with said heater.

4. The gas sensor of claim 1, wherein said sensor comprises a first lead in electrical communication with a second interior pump electrode, a second lead in electrical communication with said interior pump electrode and said second emf electrode, a third lead in electrical communication with said first emf electrode, a fourth lead in electrical communication with said exterior pump electrode, a second exterior pump electrode and said heater, a fifth lead in electrical communication with said first and second reference electrodes and a sixth lead in electrical communication with said heater.

5. The gas sensor of claim 1, wherein said air channel comprises a porous material.

6. The gas sensor of claim 1, wherein said air channel is in fluid communication with said interior pump electrode, said first emf electrode, and said second emf electrode.

* * * * *